US00PP10084P

United States Patent [19]

Noack

[11] Patent Number: Plant 10,084

[45] Date of Patent: Oct. 28, 1997

[54] FLORIBUNDA ROSE PLANT NAMED 'FLOWER CARPET RED'

[76] Inventor: Werner Noack, Im Fenne 60, 33334 Gütersloh, Germany

[21] Appl. No.: 635,172

[22] Filed: Apr. 25, 1996

[51] Int. Cl.[6] ..... A01H 5/00

[52] U.S. Cl. ..... Plt./28

[58] Field of Search ..... Plt./1, 22, 27, Plt./28

*Primary Examiner*—Howard J. Locker

*Attorney, Agent, or Firm*—Burns, Doane, Swecker & Mathis, L.L.P.

[57] ABSTRACT

A new and distinct variety of Floribunda rose plant is provided which forms continuously throughout the season attractive long-lasting light to medium red blossoms. The blossoms open on a reliable basis and well retain their attractiveness upon aging. The new variety exhibits a low, upright, and dense growth habit that renders it well suited for growing as attractive ornamentation in the landscape. The foliage is dark green and glossy and contrasts well with the light to medium red blossoms. The new variety propagates well from cuttings, by the budding of an eye, and by grafting. Excellent resistance to blackspot, mildew, and rust are exhibited.

1 Drawing Sheet

SUMMARY OF THE INVENTION

The new variety of Floribunda rose plant of the present invention was created by artificial pollination wherein two parents were crossed which previously had been studied in the hope that they would contribute the desired characteristics. Such breeding program was carried out a Gütersloh, Germany during 1986. The female parent (i.e., the seed parent) was the product of the cross of the 'Irish Wonder' variety (U.S. Plant Pat. No. 2,424) and the 'Paprika' variety (non-patented in the United States). The 'Irish Wonder' variety sometimes is known as the 'Evelyn Fison' variety, and the 'Paprika' variety sometimes is known as the 'Tanprik' variety. The male parent (i.e., the pollen parent) was the 'Flower Carpet' variety (U.S. Plant Pat. No. 7,282). The 'Flower Carpet' variety sometimes is known as the 'Noatraum' variety and is marketed under the Heidetraum trademark in Germany. The parentage of the new variety can be summarized as follows:

('Irish Wonder'×'Paprika')×'Flower Carpet'.

The seeds resulting from the above pollination were sown and small plants were obtained which physically and biologically differ from each other. Selective study resulted in the identification of a single plant of the new variety.

It is found that the new Floribunda rose plant possesses the following combination of characteristics:

(a) forms continuously throughout the season attractive light to medium red, medium-sized long-lasting blossoms which tend to open on a reliable basis and to retain their attractiveness upon aging,
(b) exhibits an upright, dense and bushy growth habit,
(c) forms attractive dark green and glossy foliage that contrasts well with the light to medium red blossoms,
(d) exhibits excellent disease resistance with respect to blackspot, mildew, and rust, and
(e) is particularly suited for growing as attractive ornamentation in the landscape.

The new variety meets the needs of the horticultural industry and can be grown to advantage as decorative ornamentation in parks, gardens, public areas, and residential landscapes.

The new variety of the present invention has been found to readily undergo asexual reproduction in Germany by the use of cuttings, by the budding of an eye, and by grafting. Such asexual reproduction as performed in Germany has shown that the characteristics of the new variety are homogeneous and stable and are strictly transmissible from one generation to another.

The new variety has been named the 'Flower Carpet Red' variety. The new variety also is known as the 'Noafeuer' variety in Europe and is being marketed under the Heidefeuer trademark in Europe.

BRIEF DESCRIPTION OF THE PHOTOGRAPH

The accompanying photograph shows as nearly true as it is reasonably possible to make the same, in a color illustration of this character, a typical specimen of the new variety while growing in the landscape. The illustrated Floribunda rose plant was three years of age and was observed during June, 1994 while growing outdoors on *Rosa laxa* understock at Gütersloh, Germany. A profusion of blossoms and the foliage of the new variety are visible wherein the buds and blossoms are shown in various stages of opening.

DETAILED DESCRIPTION

Figure 1:
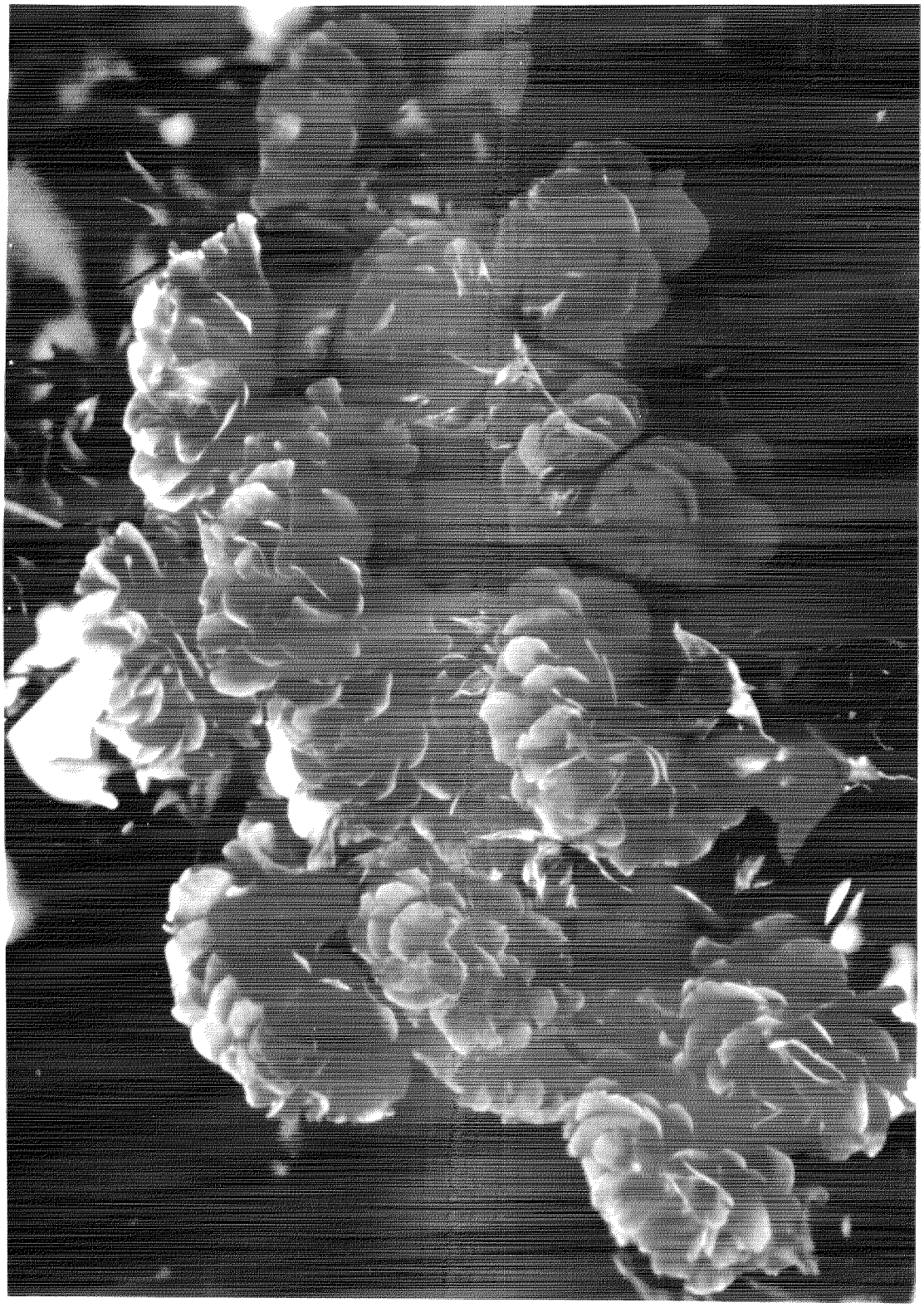

The chart used in the identification of the colors is that of The Royal Horticultural Society (R.H.S. Colour Chart) of London, England. Color terminology in common terms sometimes is included as an aid to the reader. The description is based on the observation of three year-old specimens of the new variety while growing outdoors on *Rosa laxa* understock during July at Gütersloh, Germany.

Class: Floribunda.

Parentage:

*Female.*—The cross of the 'Irish Wondor' variety (U.S. Plant Pat. No. 2,424) and the 'Paprika' variety (non-patented in the United States).

*Male.*—The 'Flower Carpet' variety (U.S. Plant Pat. No. 7,282).

Plant:

*Height.*—Approximately 50 to 60 cm. on average at the end of the growing season.

*Form.*—Vigorous, low, upright, dense, compact and bushy. The growth habit generally corresponds to that of an ideal Floribunda.

Branches:

*Color.*—Young stems: green with a smooth surface. Adult wood: medium green, Green Group 137C, with a smooth surface.

*Thorns.*—Size: medium, approximately 5 mm. in length on average, and slightly curved downward. Frequency: irregular. Over a length of 10 cm. approximately 6 thorns commonly are present. Color: initially light brown changing to dark brown, Greyed-Red Group 182A, with maturity.

Leaves:

*Stipules.*—Color: light green.

*Leaflets.*—Number: commonly 5. Quantity: very abundant. Size: commonly approximately 4 cm. in length and approximately 3 cm. in width. Serration: regular. Color (young foliage): Upper surface: reddish. Under surface: slightly lighter than upper surface. Color (adult foliage): Upper surface: dark green, Green Group 135B. Under surface: lighter than upper surface, Green Group 135C. General appearance: dense, dark green, and glossy on upper surface, and matte appearance on under surface. Configuration: long and pointed. Texture: leathery. Petioles: Green Group 138A in coloration. Stipules: Green Group 138A to 138B in coloration.

Inflorescence:

*Number of flowers.*—Numerous and commonly sprays. A two year-old plant commonly will form approximately 50 blossoms that are borne in approximately 3 to 4 sprays.

*Peduncle.*—Smooth, commonly without prickles, and commonly green on younger growth and red on older growth, and approximately 3 cm. in length on average.

*Sepals.*—Commonly extend beyond the bud up to approximately 2 cm. and are pointed, and commonly are Green Group 138A to 138B in coloration.

*Buds.*—Shape: generally pointed as shown in the photograph. Size: commonly are approximately 3.5 cm. in length. Color when opening: as the sepals divide pure red, Red Group 50A.

*Flower.*—Form: initially cup-shaped with flattening upon maturity. Diameter: approximately 5 cm. on average when fully expanded, and borne in sprays. Color (when opening begins): Upper surface: pure red, Red Group 50A. Under surface: slightly lighter than upper surface, Red Group 51A. Color (when blooming): Red Group 52A to 52C with the exception that a yellow area, Yellow Group 13A to 13B, adjacent the point of petal attachment may become visible. The yellow coloration of pollen and reproductive organs also commonly is exposed as the petals open more fully. When visible, this contrasts attractively with the pure red coloration of the petals. Color (at end of opening): the coloration lightens somewhat to near Red-Purple Group 57A immediately prior to petal drop. Fragrance: none. Lasting quality: long, approximately 4 to 5 days for a single bloom on the plant, and approximately 3 days when cut and placed in a vase. A spray commonly will last up to approximately 4 weeks. The lives of the blossoms vary somewhat with the month of the year and the environmental conditions that are encountered. Petal form: the edges tend to be relatively straight and substantially even, the shape is elliptical, and the blossom center initially is well covered by the petals. Petaloids: commonly none. Petal number: approximately 25 on average. Petal appearance: satiny on both surfaces. Petal arrangement: generally arranged in a regular pattern with overlapping edges. Petal texture: average. Petal drop: good with a clean disengagement of the petals upon full maturity. Stamens: somewhat regularly arranged around the styles, Yellow Group 12A in coloration. Filaments: nearly transparent in appearance. Pollen: yellow in coloration. Stigmas: cream yellow in coloration. Styles: thin, bunched, and tend to be of substantially the same length. Hips: oval, medium in size, and red-brown in coloration.

Development:

*Vegetation.*—Vigorous and abundant.

*Blooming.*—Abundant and substantially continuous throughout the season.

*Winter hardiness.*—Good, when reproduced by the budding of an eye the new variety has withstood a winter temperature of −20° C.

*Resistance to diseases.*—Excellent with respect to blackspot, mildew, and rust.

I claim:

1. A new and distinct variety of Floribunda rose plant characterized by the following combination of characteristics:

(a) forms continuously throughout the season attractive light to medium red, medium-sized, long-lasting blossoms which tend to open on a reliable basis and to retain their attractiveness upon aging,
(b) exhibits an upright, dense, and bushy growth habit,
(c) forms attractive dark green and glossy foliage that contrasts well with the light to medium red blossoms,
(d) exhibits excellent disease resistance with respect to blackspot, mildew, and rust, and
(e) is particularly suited for growing as attractive ornamentation in the landscape;

substantially as herein shown and described.

* * * * *

UNITED STATES PATENT AND TRADEMARK OFFICE

CERTIFICATE OF CORRECTION

PATENT NO. : PP 10,084
DATED : October 28, 1997
INVENTOR(S) : Werner Noack

It is certified that error appears in the above-identified patent and that said Letters Patent is hereby corrected as shown below:

Title page,
Item [54], Title, delete "FLOWER CARPET RED" and insert -- NOATRAUM RED --.

Column 1,
Line 15, delete "Flower Carpet" and insert -- Noatraum --.
Lines 16-17, delete "The 'Flower Carpet' variety sometimes is known as the 'Noatraum' variety and is" and insert -- The 'Noatraum' variety is also --.
Line 21, delete "'Flower Carpet'" and insert -- 'Noatraum' --.

Column 2,
Line 8, delete "'Flower Carpet Red'" and insert -- 'Noafeur' --.
Line 9, delete "'Noafeuer'" and insert -- 'Noafeur' --.
Line 41, delete "'Flower Carpet'" and insert -- 'Noatraum' --.

Signed and Sealed this

Fourteenth Day of March, 2006

JON W. DUDAS
*Director of the United States Patent and Trademark Office*